(12) United States Patent
Araki et al.

(10) Patent No.: US 9,486,652 B2
(45) Date of Patent: Nov. 8, 2016

(54) GEL COMPOSITION AND COSMETIC

(75) Inventors: Hidefumi Araki, Yokohama (JP); Kei Watanabe, Yokohama (JE); Yasunari Nakama, Yokohama (JP); Teruhiko Hineno, Yokohama (JP); Tomohiro Ilmura, Ichihara (JP); Tadashi Okawa, Ichihara (JP)

(73) Assignees: SHISEIDO COMPANY LTD., Tokyo (JP); DOW CORNING TORAY CO., Tokyo (JP)

(*) Notice: Subject to any disclaimer, the term of this patent is extended or adjusted under 35 U.S.C. 154(b) by 1671 days.

(21) Appl. No.: 12/670,410

(22) PCT Filed: Jul. 24, 2008

(86) PCT No.: PCT/JP2008/063303
§ 371 (c)(1),
(2), (4) Date: Jan. 25, 2010

(87) PCT Pub. No.: WO2009/025146
PCT Pub. Date: Feb. 26, 2009

(65) Prior Publication Data
US 2010/0190871 A1    Jul. 29, 2010

(30) Foreign Application Priority Data

Jul. 26, 2007  (JP) .................... 2007-194741

(51) Int. Cl.
*A61K 8/89*     (2006.01)
*A61Q 19/00*    (2006.01)
*A61K 8/04*     (2006.01)
*A61K 8/34*     (2006.01)
*A61K 8/891*    (2006.01)
*C08K 5/05*     (2006.01)
*A61K 8/58*     (2006.01)
*C08G 77/04*    (2006.01)
*C08G 77/14*    (2006.01)
*A61Q 1/10*     (2006.01)
*A61Q 1/02*     (2006.01)
*A61Q 17/04*    (2006.01)
*C08G 77/12*    (2006.01)

(52) U.S. Cl.
CPC ............ *A61Q 19/007* (2013.01); *A61K 8/042* (2013.01); *A61K 8/34* (2013.01); *A61K 8/585* (2013.01); *A61K 8/891* (2013.01); *C08G 77/045* (2013.01); *C08G 77/14* (2013.01); *C08K 5/05* (2013.01); *A61K 2800/544* (2013.01); *A61Q 1/02* (2013.01); *A61Q 1/10* (2013.01); *A61Q 17/04* (2013.01); *C08G 77/12* (2013.01)

(58) Field of Classification Search
CPC ... C08K 5/05; C08L 83/06; A61K 2800/544; A61K 8/042; A61K 8/34
See application file for complete search history.

(56) References Cited

U.S. PATENT DOCUMENTS

| 4,822,602 A | * | 4/1989 | Sabatelli ........................ 424/65 |
| 5,160,732 A | * | 11/1992 | Katsoulis et al. ............. 424/68 |
| 6,184,407 B1 | | 2/2001 | Yoshitake et al. |
| 2001/0051171 A1 | | 12/2001 | Mondet |

FOREIGN PATENT DOCUMENTS

| EP | 1031592 | | 8/2000 |
| JP | 2002-212427 | * | 7/2002 |
| JP | 2005-154678 | * | 6/2005 |
| WO | 2006/137576 | | 12/2006 |

OTHER PUBLICATIONS

Kageshima et al., "Application of carboxyl-modified silicone as surfactant in cosmetic field," J. Soc. Cosmet. Chem. Japan vol. 37, No. 4, 2003, pp. 309-314 and partial translation, two pages.
Fukushima, Physical chemistry of cetyl alcohol (Fragrance Journal Ltd.), Ch. 6, pp. 76-88 and partial translation, two pages.
Kageshima et al., "Application of carboxyl-modified silicone as surfactant in emulsification," Fragrance Journal extra edition 19 (2005) pp. 125-130 and partial translation, four pages.
International Preliminary Report on Patentability for corresponding PCT/JP2008/063303 mailed Feb. 18, 2010, eight pages.
Japanese Patent Abstract Publication No. 2001-213885 published Aug. 7, 2001, 15 pages.
Japanese Patent Abstract Publication No. 2008-266285 published Nov. 6, 2008, 40 pages.
Japanese Patent Abstract Publication No. 2001-200160 published Jul. 24, 2001, 13 pages.
Japanese Patent Abstract Publication No. 08-109263 published Apr. 30, 1996, 21 pages.

(Continued)

*Primary Examiner* — Alma Pipic
(74) *Attorney, Agent, or Firm* — Rankin, Hill & Clark LLP (57) ABSTRACT

The present invention provides a gel composition having improved texture in use. A gel composition consisting of an organosiloxane derivative represented by the following formula (1) or (3), a monohydric aliphatic alcohol having 10 to 30 carbon atoms, and water.

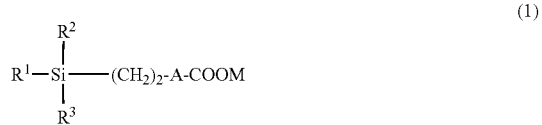

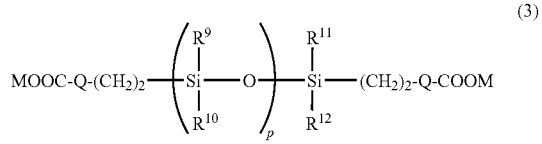

16 Claims, 2 Drawing Sheets (56) References Cited

OTHER PUBLICATIONS

Japanese Patent Abstract Publication No. 2005-154678 published Jun. 16, 2005, 14 pages.
Japanese Patent Abstract Publication No. 09-165317 published Jun. 24, 1997, 16 pages.
Japanese Patent Abstract Publication No. 2002-154917 published May 28, 2002, 21 pages.
Japanese Patent Abstract Publication No. 2006-056861 published Mar. 2, 2006, 41 pages.
Japanese Patent Abstract Publication No. 2002-212427 published Jul. 31, 2002, 12 pages.

* cited by examiner

GEL COMPOSITION AND COSMETIC

RELATED APPLICATIONS

This application claims the priority of Japanese Patent Application No. 2007-194741 filed on Jul. 28, 2007, which is incorporated herein by reference.

FIELD OF THE INVENTION

The present invention relates to a gel composition and a cosmetic comprising the same, particularly to improvement of their texture in use.

BACKGROUND OF THE INVENTION

Heretofore, organo(poly)siloxanes having various organic groups introduced in a portion of their structures have been developed by use of properties specific to dimethylpolysiloxane typified by silicone oil.

Of them, organopolysiloxane having a hydrophilic organic group introduced therein (e.g., polyoxyethylene/polysiloxane copolymers) has both hydrophilic-hydrophobic moieties in addition to hydrophobicity derived from the siloxane site and exhibits excellent surface activities. Therefore, such organopolysiloxane is generally used as a silicone-based surfactant, particularly in the field of cosmetics.

Various compounds have been developed and studied so far, for example, as organo(poly)siloxane derivatives having a carboxyl group, which is a hydrophilic organic group. As typical examples, organosiloxane derivatives having a carboxyl group introduced in the side chain of a linear polysiloxane structure are widely known. In recent years, siloxane dendrimers having a carboxyl structure have been reported as one example of such compounds (see e.g., Patent Literatures 1 to 3). Furthermore, it has also been reported that a compound obtained by neutralizing carboxyl-modified silicone with triethanolamine has an emulsification capacity (see e.g., Non-Patent Literatures 1 and 2).

On the other hand, in the field of cosmetics, it has heretofore been known that a gel structure is formed in a surfactant/higher alcohol/water system (see e.g., Non-Patent Literature 3). Cosmetics provided with excellent texture in use by the collapse of the gel structure, etc., are being developed. However, all the conventional gel compositions were less than satisfactory in terms of texture in use, due to problems such as formation of a relatively rigid gel structure. Thus, use of the silicone-based surfactants is expected to produce the effect of further improving texture in use such as skin penetration and stickiness. However, none of the conventional silicone-based surfactants are known to form a gel structure in the surfactant/higher alcohol/water system.

Patent Literature 1: Japanese Unexamined Patent Publication 2000-072784

Patent Literature 2: Japanese Unexamined Patent Publication 2000-239390

Patent Literature 3: Japanese Unexamined Patent Publication 2001-213885

Non-patent Literature 1: Kazuki KAGESHIMA and Toshiyuki SHIMIZU, "Application of carboxyl-modified silicone as surfactant in emulsification," *Fragrance Journal* extra edition 19 (2005): 125-130

Non-patent Literature 2: Kazuki KAGESHIMA, Harumi SAKAMOTO, and Toshiyuki SHIMIZU, "Application of carboxyl-modified silicone as surfactant in cosmetic field," *Journal of SCCJ* Vol. 34 No. 4 (2003): 309-314

Non-patent Literature 3: Seiji FUKUSHIMA, *Physical chemistry of cetyl alcohol* (FRAGRANCE JOURNAL LTD.) Ch. 6, 76-88.

DISCLOSURE OF THE INVENTION

Problem to be Solved by the Invention

The present invention has been conducted in view of the problems of the prior art, and an object of the present invention is to provide a gel composition having improved texture in use and a cosmetic comprising the same.

Means to Solve the Problem

To solve the problems of the prior art, the present inventors have studied diligently and consequently completed the present invention by finding that use of a specifically structured organosiloxane derivative having a carboxyl group can form a gel structure in the organosiloxane derivative/higher alcohol/water system, and the obtained gel composition offers excellent texture in use.

Specifically, a first subject of the present invention is a gel composition comprising an organosiloxane derivative represented by the following formula (1) or (3), a monohydric aliphatic alcohol having 10 to 30 carbon atoms, and water.

(1)

In the formula (1), at least one of $R^1$ to $R^3$ is a functional group represented by $-O-Si(R^4)_3$ in which $R^4$ is an alkyl group having 1 to 6 carbon atoms or a phenyl group, or a functional group represented by $-O-Si(R^5)_2-X^1$ in which $R^5$ is an alkyl group having 1 to 6 carbon atoms or a phenyl group, and $X^1$ is a functional group represented by the following formula (2) when i=1; and the remaining $R^1$ to $R^3$ may be the same or different and each may be a substituted or unsubstituted monovalent hydrocarbon group; M is a hydrogen atom, a metal atom, or an organic cation; A is a linear or branched alkylene group represented by $C_qH_{2q}$ in which q is any integer of 0 to 20; and the organosiloxane derivative represented by the formula (1) contains a total of 2 to 20 silicon atoms (Si) on average per molecule.

(2)

In the formula (2), $R^6$ is a hydrogen atom, an alkyl group having 1 to 6 carbon atoms, or a phenyl group; $R^7$ and $R^8$ are respectively an alkyl group having 1 to 6 carbon atoms or a phenyl group; B is a linear or branched alkylene group represented by $C_rH_{2r}$ which may be partially branched in which r is any integer of 2 to 20; and i specifies the generation of a silylalkyl group represented by $X^i$ and is any integer of 1 to n when the generation number is n, wherein the generation number n is any integer of 1 to 10; ai is any integer of 0 to 2 when i is 1, and is an integer smaller than 3 when i is 2 or larger; and $X^{i+1}$ is the silylalkyl group when i is smaller than n, and is a methyl group when i=n.

In the formula (3), $R^9$ to $R^{12}$ may be the same or different and are respectively a substituted or unsubstituted monovalent hydrocarbon group; M is a hydrogen atom, a metal atom, or an organic cation; Q is a linear or branched alkylene group represented by $C_qH_{2q}$ in which q is any integer of 0 to 20; and p is any number of 0 to 20.

Moreover, in the gel composition, it is preferred that the organosiloxane derivative should be represented by the formula (1), wherein $R^1$ and $R^2$ are respectively a functional group represented by —O—$Si(R^4)_3$ in which $R^4$ is an alkyl group having 1 to 6 carbon atoms; $R^3$ is a monovalent hydrocarbon group having 1 to 10 carbon atoms; and q is any integer of 6 to 20.

Moreover, in the gel composition, it is preferred that the organosiloxane derivative should be represented by the formula (1), wherein at least one or more of $R^1$ to $R^3$ are respectively a functional group represented by the following formula (4) or (5), and the remaining $R^1$ to $R^3$ may be the same or different and are respectively a substituted or unsubstituted monovalent hydrocarbon group.

Moreover, in the gel composition, it is preferred that the organosiloxane derivative should be represented by the formula (3), wherein $R^9$ to $R^{12}$ are respectively a group selected from the group consisting of substituted or unsubstituted alkyl groups having 1 to 20 carbon atoms, aryl groups, and aralkyl groups; q is any integer of 6 to 20; p is any number of 1 to 20; and M is an atom selected from the group consisting of hydrogen, alkali metal, and alkaline-earth metal atoms.

Moreover, in the gel composition, it is preferred that the monohydric aliphatic alcohol having 10 to 30 carbon atoms should be an aliphatic alcohol having a melting point of 40° C. or higher.

Moreover, a second subject of the present invention is a cosmetic comprising an organosiloxane derivative represented by the formula (1) or (3), a monohydric aliphatic alcohol having 10 to 30 carbon atoms, and water, wherein a system consisting of the organosiloxane derivative/higher alcohol/water forms a gel structure.

Moreover, in the cosmetic, it is preferred that the organosiloxane derivative should be represented by the formula (1), wherein $R^1$ and $R^2$ are respectively a functional group represented by —O—$Si(R^4)_3$ in which $R^4$ is an alkyl group having 1 to 6 carbon atoms; $R^3$ is a monovalent hydrocarbon group having 1 to 10 carbon atoms; and q is any integer of 6 to 20.

Moreover, in the cosmetic, it is preferred that the organosiloxane derivative should be represented by the formula (1), wherein at least one or more of $R^1$ to $R^3$ are respectively a functional group represented by the formula (4) or (5), and the remaining $R^1$ to $R^3$ may be the same or different and are respectively a substituted or unsubstituted monovalent hydrocarbon group.

Moreover, in the cosmetic, it is preferred that the organosiloxane derivative should be represented by the formula (3), wherein $R^9$ to $R^{12}$ are respectively a group selected from the group consisting of substituted or unsubstituted alkyl groups having 1 to 20 carbon atoms, aryl groups, and aralkyl groups; q is any integer of 6 to 20; p is any number of 1 to 20; and M is an atom selected from the group consisting of hydrogen, alkali metal, and alkaline-earth metal atoms.

Moreover, in the cosmetic, it is preferred that the monohydric aliphatic alcohol having 10 to 30 carbon atoms should be an aliphatic alcohol having a melting point of 40° C. or higher.

Effect Of The Invention

According to the present invention, use of a specifically structured organosiloxane derivative having a carboxyl group can form a gel structure in the organosiloxane derivative/higher alcohol/water system. Thus, a gel composition having excellent texture in use can be obtained.

BEST MODE FOR CARRYING OUT THE INVENTION

Hereinafter, the preferred embodiments of the present invention will be described.

A gel composition according to the present invention comprises a specifically structured organosiloxane derivative having a carboxyl group, a monohydric aliphatic alcohol having 10 to 30 carbon atoms, and water.

Organosiloxane Derivative

The organosiloxane derivative used in the present invention is a compound represented by the formula (1) or (3).

First, the organosiloxane derivative represented by the following formula (1) will be described.

The organosiloxane derivative represented by the formula (1) is an organosiloxane derivative modified with an alylcarboxyl group and having a total of 2 to 20 silicon atoms on average per molecule.

In the formula (1), at least one of $R^1$ to $R^3$ is a functional group represented by —O—Si($R^4$)$_3$ in which $R^4$ is an alkyl group having 1 to 6 carbon atoms or a phenyl group, or a functional group represented by —O—Si($R^5$)$_2$—$X^1$ in which $R^5$ is an alkyl group having 1 to 6 carbon atoms or a phenyl group, and $X^1$ is a functional group represented by the following formula (2) when i=1. In this context, all of $R^1$ to $R^3$ may respectively be any of the functional groups. Alternatively, when at least one of $R^1$ to $R^3$ is any of the functional groups, the remaining $R^1$ to $R^3$ may be the same or different and each may be a substituted or unsubstituted monovalent hydrocarbon group.

In the functional group represented by —O—Si($R^4$)$_3$, $R^4$ is an alkyl group having 1 to 6 carbon atoms or a phenyl group. Examples of the alkyl group having 1 to 6 carbon atoms include linear, branched, or cyclic alkyl groups such as methyl, ethyl, n-propyl, i-propyl, n-butyl, i-butyl, s-butyl, t-butyl, pentyl, neopentyl, cyclopentyl, and hexyl. Examples of the functional group represented by —O—Si($R^4$)$_3$ include —O—Si($CH_3$)$_3$, —O—Si($CH_3$)$_2$($C_2H_5$), —O—Si($CH_3$)$_2$($C_3H_7$), —O—Si($CH_3$)$_2$($C_4H_9$), —O—Si($CH_3$)$_2$($C_5H_{11}$), —O—Si($CH_3$)$_2$($C_6H_{13}$), —O—Si($CH_3$)$_2$($C_6H_5$). In this context, the functional group is preferably a trialkylsiloxy group, most preferably a trimethylsiloxy group.

Moreover, the functional group represented by —O—Si($R^5$)$_2$—$X^1$ is an organosiloxy group having a dendrimer structure. $R^5$ is an alkyl group having 1 to 6 carbon atoms or a phenyl group. Moreover, $X^1$ is a functional group represented by the following formula (2) when i=1.

(2)

In the formula (2), $R^6$ is a hydrogen atom, an alkyl group having 1 to 6 carbon atoms, or a phenyl group, and $R^7$ and $R^8$ are respectively an alkyl group having 1 to 6 carbon atoms or a phenyl group. $R^6$ to $R^8$ are respectively preferably an alkyl group having 1 to 6 carbon atoms, particularly preferably a methyl group. Moreover, B is a linear or branched alkylene group represented by $C_rH_{2r}$, which may be partially branched, and r is any integer of 2 to 20. Examples of the alkylene group having 2 to 20 carbon atoms, represented by B include: linear alkylene groups such as ethylene, propylene, butylene, and hexylene groups; and branched alkylene groups such as methylmethylene, methylethylene, 1-methylpentylene, and 1,4-dimethylbutylene groups. Among them, an ethylene or hexylene group is preferable.

In the formula (2), i specifies the generation of a silylalkyl group represented by $X^i$ and is any integer in the range of 1 to n when the generation number, i.e., the number of repetitions of the silylalkyl group, is n. The generation number n is any integer of 1 to 10. $X^{i+1}$ is the silylalkyl group when is smaller than n, and is a methyl group (—$CH_3$) when i=n. ai is any integer of 0 to 2 when i=1, and is a number smaller than 3 when i is 2 or larger. ai is preferably 1 or smaller, particularly preferably 0.

Specifically, when the generation n of the dendrimer structure is 1, the silylalkyl group of the formula (2) is represented by the following formula.

When the generation n of the dendrimer structure is 2, the silylalkyl group of the formula (2) is represented by the following formula.

When the generation n of the dendrimer structure is 3, the silylalkyl group of the formula (2) is represented by the following formula.

Particularly preferable examples of the functional group represented by —O—Si($R^5$)$_2$—$X^1$ include a functional group represented by the following formula (4) wherein the generation number n of the silylalkyl group is 1, and a functional group represented by the following formula (5) wherein the generation number n of the silylalkyl group is 2.

(4)

-continued (5)

Moreover, in the formula (1), as long as at least one of $R^1$ to $R^3$ is the functional group represented by —O—Si$(R^4)_3$ or the functional group represented by —O—Si$(R^5)_2$—$X^1$, the remaining $R^1$ to $R^3$ may be the same or different and each may be a substituted or unsubstituted monovalent hydrocarbon group. Examples of the unsubstituted monovalent hydrocarbon group as $R^1$ to $R^3$ include: linear, branched, or cyclic alkyl groups such as methyl, ethyl, n-propyl, i-propyl, n-butyl, i-butyl, s-butyl, pentyl, neopentyl, cyclopentyl, and hexyl; aryl groups such as phenyl, tolyl, and, xylyl groups: and aralkyl groups. Examples of the substituted monovalent hydrocarbon group as $R^1$ to $R^3$ include: perfluoroalkyl groups such as 3,3,3-trifluoropropyl and 3,3,4,4,4-pentafluorobutyl groups; aminoalkyl groups such as 3-aminopropyl and 3-(aminoethyl)aminopropyl groups; and amidoalkyl groups such as acetylaminoalkyl groups. Moreover, the hydrocarbon group as $R^1$ to $R^3$ may be partially substituted by a hydroxyl, alkoxy, polyether, or perfluoropolyether group. Examples of the alkoxy group include methoxy, ethoxy, and propoxy groups.

In the formula (1), when one or two of $R^1$ to $R^3$ are respectively the functional group represented by —O—Si$(R^4)_3$ or the functional group represented by —O—Si$(R^5)_2$—$X^1$, the remaining $R^1$ to $R^3$ are respectively preferably a linear or branched alkyl group having 1 to 6 carbon atoms, particularly preferably a methyl or ethyl group. Particularly, in the formula (1), it is preferred that all or two of $R^1$ to $R^3$ should respectively be the functional group represented by —O—Si$(R^4)_3$ or the functional group represented by —O—Si$(R^5)_2$—$X^1$, and the remaining $R^1$ to $R^3$ should be a methyl or ethyl group.

Moreover, M is a hydrogen atom, a metal atom, or an organic cation. Examples of the metal atom include monovalent alkali metals, divalent alkali metals, and di- or higher valent metal atoms. Examples of the monovalent alkali metals include Li, Na, and K. Examples of the divalent alkali metals include Mg, Ca, and Ba. Other examples of the metal atom include Mn, Fe, Co, Al, Ni, Cu, V, Mo, Nb, Zn, and Ti. Moreover, examples of the organic cation include ammonium, monoethanolammonium, triethanolammonium, arginine-neutralized, and aminomethyl propanol (AMP)-neutralized ions. M is particularly preferably a hydrogen atom or a monovalent alkali metal or may be a mixture thereof.

A is a linear or branched alkylene group represented by $C_qH_{2q}$, and q is any integer of 0 to 20. In this context, when q=0, the organosiloxane derivative represented by the formula (1) is a compound represented by the following formula (1'), wherein the carboxyl-modified group is bound with silicon via an ethylene group. In the present invention, q is preferably any integer of 2 to 15, more preferably any integer of 6 to 12. On the other hand, if q exceeds the upper limit, the resulting gel composition offers poor texture in use.

$R^1R^2R^3Si$—$(CH_2)_2$—COOM  (1')

Moreover, the organosiloxane derivative represented by the formula (1) is characterized by containing a total of 2 to 20 silicon atoms on average per molecule. The organosiloxane derivative represented by the formula (1) contains preferably a total of 3 to 18 silicon atoms on average, particularly preferably a total of 3 to 7 silicon atoms on average. On the other hand, if the total number of the silicon atoms per molecule exceeds the upper limit, a gel structure may not be formed in the organosiloxane derivative/higher alcohol/water system.

The organosiloxane derivative represented by the formula (1) that can be used preferably is more specifically an organosiloxane derivative wherein $R^1$ and $R^2$ are respectively a functional group represented by —O—Si$(R^4)_3$ in which $R^4$ is an alkyl group having 1 to 6 carbon atoms; $R^3$ is a linear or branched alkyl group having 1 to 6 carbon atoms; and q is any integer of 6 to 12.

The organosiloxane derivative represented by the formula (1) can be produced by the steps of causing addition reaction between polysiloxane containing a silicon-bound hydrogen atom, represented by $R^1R^2R^3SiH$ and a trimethylsilyl carboxylate derivative having a vinyl end, represented by CH=$CH_2$-A-COOSiMe$_3$ in the presence of a platinum-based catalyst, adding, to the reaction product, at least 1 mol or more of a monohydric alcohol (e.g., methanol), water, or a mixture thereof per mol of the trimethylsilyl group as a protective group, and heating the mixture to deprotect the protective group by alcoholysis. In this context, $R^1$, $R^2$, $R^3$, A, and M are as defined above. When M is a metal atom or an organic cation, the production method further comprises a neutralization step using a compound containing the corresponding metal ion (M$^{n+}$) or a basic organic compound. As an example, such a step is the step of neutralizing the carboxyl group (—COOH) by the addition of an aqueous solution of sodium hydroxide (NaOH), potassium hydroxide (KOH), triethanolamine, arginine, aminomethyl propanol (AMP), or the like.

Moreover, the method for producing the organosiloxane derivative represented by the formula (1) is described in detail in Japanese Unexamined Patent Publication Nos. 2000-072784, 2000-239390, and 2001-213885. The organosiloxane derivative of the present invention represented by the formula (1) can be produced easily, particularly by a production method comprising the following steps (1) to (3).

Step (1):

The step of causing addition reaction between organosilane having a dimethylsiloxy group, represented by HSi(—O—SiR$_2$H)$_f$R$^L_{3-f}$ (wherein R is an alkyl group having 1 to 6 carbon atoms or a phenyl group; R$^L$ may be the same or different and is a substituted or unsubstituted monovalent hydrocarbon group; and f is any integer of 1 to 3) and a trimethylsilyl carboxylate derivative having a vinyl end, represented by CH=$CH_2$-A-COOSiMe$_3$ (wherein A is as defined above) in the presence of a platinum-based transition metal catalyst to obtain an intermediate (1-1) of the following formula:

Si(—O—SiR$_2$H)$_f$R$^L_{3-f}$—(CH$_2$)$_2$-A-COOSiMe$_3$  (1-1)

Step (2):

The step of causing addition reaction between organosilane having an alkenyl group, represented by R$^B$Si(O—R$^6$)$_{ai}$(OSiR$^7$R$^8$—X$^{i+1}$)$_{3-ai}$ (wherein R$^B$ is a linear or branched alkenyl group represented by C$_r$H$_{2r}$; r is any integer of 2 to 20; and R$^6$, R$^7$, R$^8$, X$^{i+1}$, and ai are as defined above) and the intermediate (1-1)

in the presence of a platinum-based catalyst to obtain an intermediate (1-2) of the following formula:

$$Si\{-O-SiR_2-B-Si(O-R^6)_{ai}(OSiR^7R^8-X^{i+1})_{3-ai}\}_fR^L{}_{3-f}(CH_2)_2\text{-}A\text{-}COOSiMe_3 \quad (1\text{-}2)$$

Step (3):

The step of adding, to the intermediate (1-2), at least 1 mol or more of a monohydric alcohol (e.g., methanol), water, or a mixture thereof per mol of the trimethylsilyl group as a protective group, and heating the mixture to deprotect the protective group by alcoholysis.

In the organosiloxane derivative represented by the formula (1), when M is a metal atom or an organic cation, the production method further comprises a neutralization step using a compound containing the corresponding metal ion ($M^{n+}$) or a basic organic compound. As an example, such a step is the step of neutralizing the carboxyl group (—COOH) by the addition of an aqueous solution of sodium hydroxide (NaOH), potassium hydroxide (KOH), triethanolamine, arginine, aminomethyl propanol (AMP), or the like.

Subsequently, the organosiloxane derivative represented by the following formula (3) will be described.

$$MOOC\text{-}Q\text{-}(CH_2)_2-\left(\begin{array}{c}R^9\\|\\Si-O\\|\\R^{10}\end{array}\right)_p\begin{array}{c}R^{11}\\|\\Si-\\|\\R^{12}\end{array}(CH_2)_2\text{-}Q\text{-}COOM \quad (3)$$

The organosiloxane derivative represented by the formula (3) is an organosiloxane derivative modified, at both ends of the molecular chain, with an alkylcarboxyl group.

In the formula (3), $R^9$ to $R^{12}$ may be the same or different and are selected from substituted or unsubstituted monovalent hydrocarbon groups. Examples of the unsubstituted monovalent hydrocarbon group represented by $R^9$ to $R^{12}$ include: linear or branched alkyl groups such as methyl, ethyl, propyl, butyl, pentyl, hexyl, heptyl, octyl, decyl, and dodecyl groups; linear or branched alkenyl groups such as allyl and hexenyl groups; cycloalkyl groups such as cyclopentyl and cyclohexyl groups; aryl groups such as phenyl, tolyl, and naphthyl groups; and aralkyl groups such as benzyl, phenylethyl, phenylpropyl, naphthylmethyl, and naphthylethyl groups. Examples of the substituted monovalent hydrocarbon group represented by $R^9$ to $R^{12}$ include groups in which hydrogen atoms bound with the carbon atoms of the hydrocarbon groups described above are partially substituted by an organic group such as a hydroxyl group, a halogen atom, an epoxy group, an amino group, a methacryl group, a mercapto group, an alkoxy group, a polyether group, or a perfluoropolyether group and specifically include: perfluoroalkyl groups such as 3,3,3-trifluoropropyl and 3,3,4,4,4-pentafluorobutyl groups; aminoalkyl groups such as 3-aminopropyl and 3-(aminoethyl)aminopropyl groups; and aminoalkyl groups such as acetylaminoalkyl groups. $R^9$ to $R^{12}$ are respectively preferably an alkyl group having 1 to 20 carbon atoms, an aryl group, or an aralkyl group. It is particularly preferred that 90% by mol or more of $R^9$ to $R^{12}$ in one molecule should be a methyl group and/or a phenyl group.

Moreover, M is a hydrogen atom, a metal atom, or an organic cation. Examples of the metal atom include monovalent alkali metals, divalent alkali metals, and di- or higher valent metal atoms. Examples of the monovalent alkali metals include Li, Na, and K. Examples of the divalent alkali metals include Mg, Ca, and Ba. Other examples of the metal atom include Mn, Fe, Co, Al, Ni, Cu, V, Mo, Nb, Zn, and Ti. Moreover, examples of the organic cation include ammonium, monoethanolammonium, triethanolammonium, arginine-neutralized, and aminomethyl propanol (AMP)-neutralized ions. M is particularly preferably a hydrogen atom or a monovalent alkali metal or may be a mixture thereof.

Q is a linear or branched alkylene group represented by $C_qH_{2q}$, and q is any integer of 0 to 20. In this context, when q=0, the organosiloxane derivative represented by the formula (3) is a compound represented by the following formula (3'), wherein the carboxyl-modified group is bound with silicon via an ethylene group. In the present invention, q is preferably any integer of 6 to 20, more preferably any integer of 6 to 12. On the other hand, if q exceeds the upper limit, the resulting gel composition offers poor texture in use.

$$MOOC-(CH_2)_2-(SiR^9R^{10}-O)_p-SiR^{11}R^{12}-(CH_2)_2-COOM \quad (3')$$

In the formula (3), p represents the average degree of polymerization of di-substituted polysiloxane and is any number of 0 to 20. In the present invention, p is more preferably any number of 1 to 20, particularly preferably any number of 1 to 10. On the other hand, if p exceeds the upper limit, a gel structure may not be formed in the organosiloxane derivative/higher alcohol/water system.

The organosiloxane derivative represented by the formula (3) that can be used preferably is an organosiloxane derivative wherein $R^9$ to $R^{12}$ are respectively an alkyl group having 1 to 6 carbon atoms; q is any integer of 0 to 20; and p is any number of 0 to 20.

The organosiloxane derivative represented by the formula (3) can be produced by the steps of causing addition reaction between organohydrogenpolysiloxane having a silicon-bound hydrogen atom at both ends of the molecular chain, represented by $$H-(SiR^9R^{10}-O)_p-SiR^{11}R^{12}-H$$

(wherein $R^9$ to $R^{12}$ are as defined above; and p is any number of 0 to 20) and at least 2 mol of a trimethylsilyl carboxylate derivative having a vinyl end, represented by $CH=CH_2$-Q-$COOSiMe_3$ with respect to 1 mol of the organohydrogenpolysiloxane in the presence of a platinum-based catalyst, adding, to the reaction product, at least 1 mol or more of a monohydric alcohol (e.g., methanol), water, or a mixture thereof per mol of the trimethylsilyl group as a protective group, and heating the mixture to deprotect the protective group by alcoholysis. In this context, when Q is as defined above and M is a metal atom or an organic cation, the production method further comprises a neutralization step using a compound containing the corresponding metal ion ($M^{n+}$) or a basic organic compound.

Specifically, such a step is the step of neutralizing the carboxyl group (—COOH) by the addition of an aqueous solution of sodium hydroxide (NaOH), potassium hydroxide (KOH), triethanolamine, arginine, aminomethyl propanol (AMP), or the like.

The platinum-based catalyst used for producing the organosiloxane derivative of the present invention represented by the formula (1) or (3) is a catalyst for hydrosilylation reaction between the silicon-bound hydrogen atom and the alkenyl group. Examples thereof include chloroplatinic acid, alcohol-modified chloroplatinic acid, olefin complexes of platinum, ketone complexes of platinum, vinylsiloxane complexes of platinum, platinum tetrachloride, fine platinum powders, solid platinum supported by an alumina or silica carrier, platinum black, olefin complexes of platinum, alkenylsiloxane complexes of platinum, carbonyl complexes of platinum, and thermoplastic organic resin (e.g., methyl methacrylate, polycarbonate, polystyrene, and silicone resins) powders containing these platinum-based catalysts. Preferably, the platinum-based catalyst is a 1,3-divinyl-1,1,3,3-tetramethyldisiloxane complex of platinum or chloroplatinic acid.

Monohydric Aliphatic Alcohol having 10 to 30 Carbon Atoms (Higher Alcohol)

Moreover, the monohydric aliphatic alcohol having 10 to 30 carbon atoms (hereinafter, also referred to as a higher alcohol simply) used in the present invention is a saturated or unsaturated monohydric aliphatic alcohol and may be linear or branched. More preferably, the higher alcohol is linear. It is also preferred that the higher alcohol should be a higher alcohol having a melting point of 40° C. or higher. If the melting point is lower than 40° C., a gel structure may not be formed. Examples of the monohydric aliphatic alcohol having 10 to 30 carbon atoms, used in the present invention include stearyl alcohol, isostearyl alcohol, oleyl alcohol, octyldodecanol, chimyl alcohol, cholesterol, sitosterol, cetanol, cetostearyl alcohol, selachyl alcohol, decyl tetradecanol, batyl alcohol, phytosterol, hexyldecanol, behenyl alcohol, lauryl alcohol, lanoline alcohol, and hydrogenated lanoline alcohol. In the present invention, it is preferred to use a higher alcohol having a melting point of 40 to 80° C. in itself or to use a plurality of higher alcohols combined to give a melting point of 40 to 70° C.

Gel Composition

In the present invention, use of the specifically structured organosiloxane derivative represented by the formula (1) or (3) can form a gel structure in the organosiloxane derivative/higher alcohol/water system. In this context, the gel structure according to the present invention is usually one kind of associate structure formed by the surfactant and is a crystal structure characterized in that bilayer membranes of the surfactant and the higher alcohol are arranged in a layer form in a long-period structure and the hydrophobic groups of the surfactant and the higher alcohol are arranged in a hexagonal form on the short-plane side. In this context, it is known that the hydrophobic groups rotate about their major axes without free thermal motion seen in liquid-crystal structures, and a large amount of water exists between the hydrophilic groups (see e.g., S., Fukushima, "Physical Chemistry of Cetyl Alcohol", Fragrance Journal Ltd., Chapter 6, p. 76-88). Compositions having such a gel structure are known to have unique texture in use and widely used, particularly in, for example, creams, cleansers, and lotions in the field of cosmetics.

In the present invention, the gel composition means a composition having a gel structure within the system. The presence or absence of the gel structure may be determined according to methods conventionally known in the art and can be determined by, for example, X-ray diffractometry. In the X-ray diffractometry conducted on a composition having the gel structure, repetitive peaks derived from long spacing as in lamella structures are usually obtained in a small-angle region while a sharp single peak derived from the hexagonal system on the short-plane side is shown around $2\theta=21.4°$ in a wide-angle region. Moreover, according to differential scanning calorimetry (DSC) measurement, an endothermic peak is observed along with melting of the crystal structure containing the gel structure. Based on this, the crystal structure may be estimated.

The gel composition according to the present invention comprises the organosiloxane derivative represented by the formula (1) or (3), the monohydric aliphatic alcohol having 10 to 30 carbon atoms, and water and is obtained as a composition having the gel structure, by mixing these components at an appropriate ratio. The mixing ratio of the components is not particularly limited as long as it allows formation of the gel structure within the system. Specifically, the molar ratio of the organosiloxane derivative: monohydric aliphatic alcohol having 10 to 30 carbon atoms is preferably in the range of 1:0.1 to 1:30, particularly preferably in the range of 1:3 1:10. If the molar ratio is not within the specified range, the gel structure may not be formed stably. Moreover, the amount of water incorporated is preferably in the range of 100 to 10000 parts by mass, particularly preferably in the range of 200 to 7000 parts by mass, with respect to 100 parts by mass of the mixture. In this context, water may be mixed therewith in two or more portions. Specifically, 100 to 1000 parts by mass of water is added with respect to 100 parts by mass of a mixture of the organosiloxane derivative and the monohydric aliphatic alcohol having 10 to 30 carbon atoms to form a stable gel structure within the system. Then, additional water can be added to the system to thereby obtain a composition having, within the system, a stable gel structure comprising the organosiloxane derivative/monohydric aliphatic alcohol having 10 to 30 carbon atoms/water.

Cosmetic

Moreover, the specifically structured organosiloxane derivative represented by the formula (1) or (3), the monohydric aliphatic alcohol having 10 to 30 carbon atoms, and water are together incorporated in a cosmetic to form a gel structure in the cosmetic preparation. The resultant cosmetic, for example, a cream, cleanser, lotion, or milky lotion, can be provided with excellent texture in use, particularly in terms of the absence of slimy feel, quick skin penetration, and the absence of stickiness.

Therefore, the cosmetic according to the present invention is characterized by comprising the organosiloxane derivative represented by the formula (1) or (3), the higher alcohol, and water, wherein a system consisting of the organosiloxane derivative/higher alcohol/water forms a gel structure.

The amount of the organosiloxane derivative incorporated in the cosmetic of the present invention is not particularly limited and is usually 0.1 to 5% by mass, preferably 0.1 to 2% by mass, more preferably 0.3 to 1% by mass, of the total amount of the composition. If the organosiloxane derivative is incorporated in too small an amount, this formulation produces no effect. Moreover, if the organosiloxane derivative is incorporated in too large an amount, it may adversely affect texture in use.

The amount of the monohydric aliphatic alcohol having 10 to 30 carbon atoms, incorporated in the cosmetic of the present invention is not particularly limited and is usually 0.1 to 10% by mass, preferably 0.1 to 5% by mass, more preferably 0.3 to 2% by mass, of the total amount of the composition. If the monohydric aliphatic alcohol having 10 to 30 carbon atoms is incorporated in too small an amount, this formulation produces no effect. Moreover, if the monohydric aliphatic alcohol having 10 to 30 carbon atoms is incorporated in too large an amount, it may adversely affect texture in use.

The cosmetic of the present invention can be formulated optionally with, in addition to the essential components, other components usually used in the cosmetic or medical field, for example, oils, waxes, moisturizers, emulsifying agents, surfactants, thickeners, gelling agents, metallic soaps, water-soluble polymers, oil-soluble polymers, drugs, antioxidants, pigments, dyes, pearlescent agents, lame agents, organic/inorganic powders, and flavors, within a qualitative/quantitative range that does not impair the effects of the present invention.

The use application of the cosmetic of the present invention is not particularly limited, and it can be used in various cosmetics, for example, skincare cosmetics (e.g., moisturizing creams, moisturizing milky lotions, moisturizing lotions, massage creams, massage lotions, and essences), hair-care cosmetics (e.g., hair creams, hair lotions, and hair dressings), body-care cosmetics (e.g., sunscreens, body creams, and body lotions), makeup cosmetics (e.g., lip sticks, mascaras, eyeliners, nail enamels, liquid foundations, and gel foundations), and cleansers (e.g., makeup removers, shampoos, hair conditioners, and two-in-one shampoos).

EXAMPLES

Hereinafter, the present invention will be described more specifically with reference to Examples. However, the present invention is not intended to be limited to them.

The structures and synthesis methods of organosiloxane derivatives (compounds 1 to 4 and comparative compounds 1 to 4) used in Examples and Comparative Examples are shown below. In this context, each compound was identified by $^1$H, $^{13}$C, $^{29}$Si-NMR (NMR apparatus: Fourier Transform Nuclear Magnetic Resonance Spectrometer JEOL JNM-EX400 (manufactured by JEOL Ltd.).

Compound 1

Synthesis Method of Compound 1

100 g of 1,1,1,3,5,5,5-heptamethyltrisiloxane and 0.02 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 100° C., 105 g of trimethylsilyl undecylenate was added dropwise to the flask. After the completion of the dropwise addition, the mixture was aged at 100° C. for 2 hours, and the completion of the reaction was then confirmed using gas chromatography. Low-boiling fractions were distilled off under reduced pressure. Then, methanol and water were added thereto, and the mixture was aged for 5 hours under reflux for deprotection. Then, low-boiling fractions were removed again under reduced pressure to obtain a compound 1. As a result of analysis, the compound 1 was confirmed to be represented by the chemical structural formula shown above.

Compound 2

Synthesis Method of Compound 2

A flask equipped with a stirrer, a thermometer, a reflux condenser, and a dropping funnel was charged with 100 g of tetrakis(dimethylsiloxy)silane and 0.02 g of a toluene solution of a platinum-1,3-divinyl-1,1,3,3-tetramethyldisiloxane complex. The mixture was heated to 90° C. with stirring. Subsequently, while the reaction temperature was kept at 90° C., 15.6 g of trimethylsilyl undecylenate was gradually added dropwise thereto using the dropping funnel. After the completion of the dropwise addition, the reaction solution was heated at 100° C. for 1 hour. After cooling, the reaction solution was distilled under reduced pressure to obtain 35.3 g of a colorless, transparent liquid. As a result of analysis, this liquid was confirmed to be a compound represented by the structural formula shown below. This compound was designated as an intermediate 2A.

Intermediate 2A

Next, 54.1 g of vinyl tris(trimethylsiloxy)silane and 0.01 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 100° C., 35 g of the intermediate 2A was added dropwise to the flask. After the completion of the dropwise addition, the mixture was aged at 100° C. for 2 hours. Then, the disappearance of the Si—H bonds was confirmed by FT-IR. Low-boiling fractions were distilled off under reduced pressure. Then, 8 g of methanol was added thereto, and the mixture was aged for 5 hours under reflux for deprotection. Then, low-boiling fractions were removed again under reduced pressure. As a result of analysis, the obtained compound was confirmed to be a compound 2 represented by the chemical structural formula shown above.

Compound 3

Synthesis Method of Compound 3

460.81 g of trimethylsilyl undecylenate and 0.05 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 80° C., 100 g of 1,1,3,3-tetramethyldisiloxane was added dropwise to the flask. After the completion of the dropwise addition, the mixture was aged at 100° C. for 2 hours, and the completion of the reaction was then confirmed using gas chromatography. Low-boiling fractions were distilled off under reduced pressure. Then, 240 g of methanol was added thereto, and the mixture was aged for 5 hours under reflux for deprotection. Then, low-boiling fractions were removed again under reduced pressure to obtain a compound 3. As a result of analysis, the compound 3 was confirmed to be represented by the chemical structural formula shown above.

Compound 4

Synthesis Method of Compound 4

225.0 g of trimethylsilyl undecylenate and 0.05 g of a toluene solution of a platinum-1,3-divinyl-1,1,3,3-tetramethyldisiloxane complex were added to a flask equipped with a stirrer, a reflux condenser, a dropping funnel, and a thermometer. While the temperature was kept in the range of 70 to 80° C., 225 g of siloxane having Si—H at both ends, represented by the following formula was added dropwise to the flask.

After the completion of the dropwise addition, the mixture was aged at 100° C. for 2 hours. Then, the disappearance of the Si—H bonds was confirmed by FT-IR. Low-boiling fractions were distilled off under reduced pressure. Then, 127 g of methanol was added thereto, and the mixture was aged for 5 hours under reflux for deprotection. Then, low-boiling fractions were removed again under reduced pressure to obtain a compound 4. As a result of analysis, the compound 4 was confirmed to be represented by the chemical structural formula shown above.

Moreover, organosiloxane derivatives as comparative compounds 1 to 4 shown below were prepared according to the synthesis methods of the compounds 1 to 4.

First, the present inventors studied the phase state of a composition in an organosiloxane derivative/higher alcohol/water system. In this context, the compound 1 was used as the organosiloxane derivative, and a 1:1 mixture of behenyl alcohol and stearyl alcohol was used as the higher alcohol. These components were mixed at varying ratios to prepare compositions, which were then subjected to differential scanning calorimetry (DSC). The detail of the test is as shown below.

Test Examples 1 to 5

An appropriate amount of potassium hydroxide was added to ion-exchanged water and dissolved at room temperature to bring the total amount to 80 parts. Subsequently, the compound 1 (hereinafter, abbreviated to $TMSC_{10}COOH$) and the 1:1 mixture of behenyl alcohol and stearyl alcohol (hereinafter, abbreviated to Be/St) were mixed at varying ratios (molar ratio) shown below, and 20 parts of this mixture was added thereto. The mixture was heated to 70° C. and mixed with stirring using a homo mixer. Then, the mixture was rapidly cooled to 30° C. Finally, the temperature was brought to room temperature to obtain compositions of Test Examples 1 to 5.

Test Example 1 Be/St:$TMSC_{10}COOK$=0.5:1
2 Be/St:$TMSC_{10}COOK$=1:1
3 Be/St:$TMSC_{10}COOK$=3:1
4 Be/St:$TMSC_{10}COOK$=5:1
5 Be/St:$TMSC_{10}COOK$=10:1

The compositions of Test Examples 1 to 5 thus obtained were respectively subjected to differential scanning calorimetry (DSC) measurement using DSC Q1000 (manufactured by TA Instruments). The DSC measurement results are shown in FIG. 1.

Figure 1:
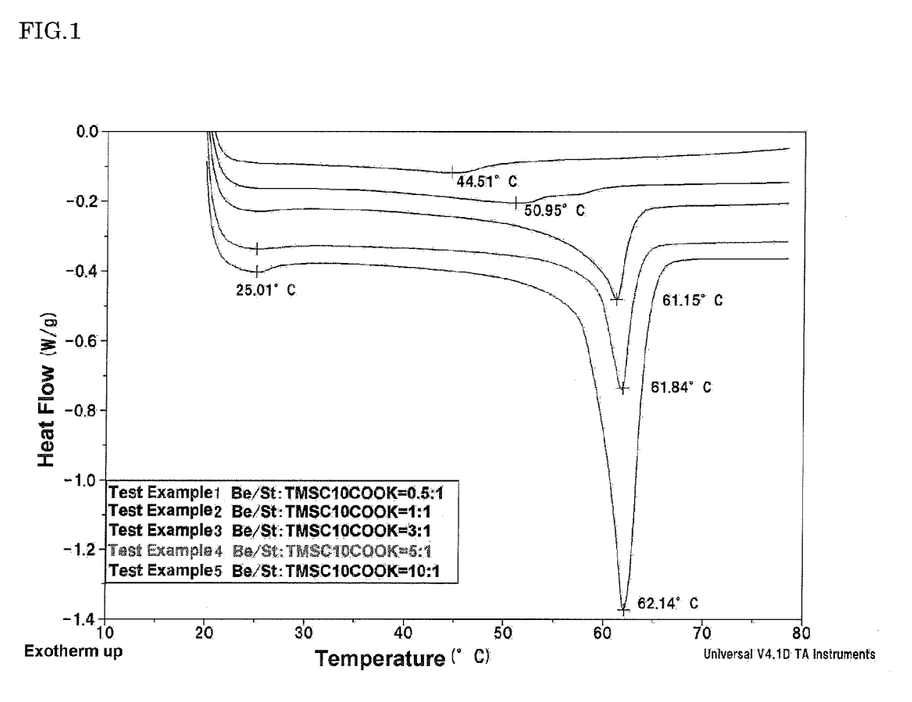
FIG. 1 shows results of differential scanning calorimetry (DSC) measurement of compositions of Test Examples 1 to 5 (Be/St:$TMSC_{10}COOH$=0.1:1 to 10:1).

As can be seen from FIG. 1, a sharp single peak probably derived from a gel structure formed by the organosiloxane derivative/higher alcohol/water was observed around 61 to 62° C. with increases in the molar ratio of behenyl alcohol/stearyl alcohol, particularly, in Test Examples 3 to 5 having 3:1 to 10:1 molar ratios of behenyl alcohol/stearyl alcohol: compound 1.

Subsequently, the present inventors examined the presence or absence of a formed gel structure using the organosiloxane derivatives as the compounds 2 to 4 and the comparative compounds 1 to 4 in the same way as in the Test Examples. In this context, a 1:1 mixture of behenyl alcohol and stearyl alcohol was used as a higher alcohol, as in the test described above. The results are summarized in Table 1 below. The evaluation was conducted according to the following criteria.

<Gel Formation>
O: an endothermic peak presumed to be a melting peak of the gel structure was observed in DSC measurement.
X: an endothermic peak corresponding to a melting peak of the gel structure was not observed in DSC measurement.

TABLE 1

| | Silicon atom number | Carboxyl group number | Gel formation |
|---|---|---|---|
| Compound 1 | 3 | 1 | O |
| Compound 2 | 16 | 1 | O |
| Compound 3 | 2 | 2 | O |
| Compound 4 | 8.6 | 2 | O |
| Comparative Compound 1 | 1 | 1 | X |
| Comparative Compound 2 | 100 | 1 | X |
| Comparative Compound 3 | 100 | 2 | X |
| Comparative Compound 4 | 104 | 4 | X |

As shown in the Table 1, the compounds 1 and 2 having an alkylcarboxyl group substituted for the side chain of trisiloxane or dendrimer-type polysiloxane as well as the compounds 3 and 4 having an alkylcarboxyl group substituted for both ends of linear disiloxane or polysiloxane were demonstrated to form a gel structure in the organosiloxane derivative/higher alcohol/water system.

By contrast, the comparative compound 1 having an alkylcarboxyl group substituted for trimethylsilane as well as the comparative compounds 2, 3, and 4 having an alkylcarboxyl group substituted for either end, both ends, or side chain of long-chain polysiloxane (Si=100) were not observed to form a gel structure even after the mixing of the higher alcohol and water.

Subsequently, the present inventors formulated with the organosiloxane derivative, a higher alcohol, and water in a cosmetic (milky lotion), which was then evaluated for its texture in use (slimy feel, skin penetration, and stickiness) and emulsion stability. The composition and evaluation results of each cosmetic used in the test are together shown in Tables 2 and 3 below. The evaluation was conducted according to criteria shown below.

Texture in use (the absence of slimy feel, quick skin penetration, and the absence of stickiness)

Ten expert panelists actually applied the cosmetic of each Test Example to their skins and evaluated the texture in use (the absence of slimy feel upon application, quick skin penetration upon application, and the absence of stickiness after application) of the cosmetic. The evaluation was conducted according to the following criteria:
⊚: of ten expert panelists, nine or more judged the cosmetic as being good.
O: of ten expert panelists, six to eight judged the cosmetic as being good.
Δ: of ten expert panelists, three to five judged the cosmetic as being good.
X: of ten expert panelists, two or less judged the cosmetic as being good.

Emulsion Stability

The cosmetic of each Test Example was prepared and then charged into a transparent glass tube, which was in turn tightly closed and stored for 1 month in a thermostat bath at 50° C. Then, the state of the emulsified particles was evaluated. The evaluation was conducted according to the following criteria:
⊚: no change in the state of the emulsified particles was observed.
O: the emulsified particles were slightly increased in size.
Δ: the emulsified particles were increased in size.
X: the emulsified particles were increased in size, resulting in separation.
XX: the cosmetic had separation immediately after production and could not be evaluated.

TABLE 2

| Milky lotion | Example 1 | Example 2 | Example 3 | Example 4 | Example 5 |
|---|---|---|---|---|---|
| Ion-exchange water | 73.4 | 73.4 | 73.4 | 73.4 | 73.4 |
| Trisodium edetate | 0.1 | 0.1 | 0.1 | 0.1 | 0.1 |
| Phenoxy ethanol | 0.3 | 0.3 | 0.3 | 0.3 | 0.3 |
| Butylene glycol | 5 | 5 | 5 | 5 | 5 |
| Glycerin | 5 | 5 | 5 | 5 | 5 |
| Carboxyvinyl polymer | 0.1 | 0.1 | 0.1 | 0.1 | 0.1 |
| Potassium hydroxide | 0.1 | 0.1 | 0.1 | 0.1 | 0.1 |
| Compound 1 | 1 | — | — | — | 0.5 |
| Compound 2 | — | 1 | — | — | 0.5 |
| Compound 3 | — | — | 1 | — | — |
| Compound 4 | — | — | — | 1 | — |
| Comparative compound 1 | — | — | — | — | — |
| Comparative compound 2 | — | — | — | — | — |
| Comparative compound 3 | — | — | — | — | — |
| Comparative compound 4 | — | — | — | — | — |
| Behenyl alcohol | 0.5 | 0.5 | 0.5 | 0.5 | 0.5 |
| Stearyl alcohol | 0.5 | 0.5 | 0.5 | 0.5 | 0.5 |
| Behenic acid | — | — | — | — | — |
| Stearic acid | — | — | — | — | — |
| Squalan | 3 | 3 | 3 | 3 | 3 |

TABLE 2-continued

| Milky lotion | | Example 1 | Example 2 | Example 3 | Example 4 | Example 5 |
|---|---|---|---|---|---|---|
| Cetyl 2-ethylhexanoate | | 3 | 3 | 3 | 3 | 3 |
| Dimethylpolysiloxane | | 5 | 5 | 5 | 5 | 5 |
| Decamethylcyclopentasiloxane | | 3 | 3 | 3 | 3 | 3 |
| Texture in use | No slimy feel | ○ | ○ | ○ | ○ | ○ |
| | Quick skin penetration | ○ | ○ | ○ | ○ | ○ |
| | No stickiness | ◎ | ○ | ○ | ○ | ◎ |
| Emulsion stability | | ◎ | ◎ | ◎ | ◎ | ◎ |

TABLE 3

| Milky lotion | Comparative example 1 | Comparative example 2 | Comparative example 3 | Comparative example 4 | Comparative example 5 | Comparative example 6 |
|---|---|---|---|---|---|---|
| Ion-exchange water | 73.4 | 73.4 | 73.4 | 73.4 | 73.4 | 74.4 |
| Trisodium edetate | 0.1 | 0.1 | 0.1 | 0.1 | 0.1 | 0.1 |
| Phenoxy ethanol | 0.3 | 0.3 | 0.3 | 0.3 | 0.3 | 0.3 |
| Butylene glycol | 5 | 5 | 5 | 5 | 5 | 5 |
| Glycerin | 5 | 5 | 5 | 5 | 5 | 5 |
| Carboxyvinyl polymer | 0.1 | 0.1 | 0.1 | 0.1 | 0.1 | 0.1 |
| Potassium hydroxide | 0.1 | 0.1 | 0.1 | 0.1 | 0.1 | 0.1 |
| Compound 1 | — | — | — | — | 1 | 1 |
| Compound 2 | — | — | — | — | — | — |
| Compound 3 | — | — | — | — | — | — |
| Compound 4 | — | — | — | — | — | — |
| Comparative compound 1 | 1 | — | — | — | — | — |
| Comparative compound 2 | — | 1 | — | — | — | — |
| Comparative compound 3 | — | — | 1 | — | — | — |
| Comparative compound 4 | — | — | — | 1 | — | — |
| Behenyl alcohol | 0.5 | 0.5 | 0.5 | 0.5 | — | — |
| Stearyl alcohol | 0.5 | 0.5 | 0.5 | 0.5 | — | — |
| Behenic acid | — | — | — | — | 0.5 | — |
| Stearic acid | — | — | — | — | 0.5 | — |
| Squalan | 3 | 3 | 3 | 3 | 3 | 3 |
| Cetyl 2-ethylhexanoate | 3 | 3 | 3 | 3 | 3 | 3 |
| Dimethylpolysiloxane | 5 | 5 | 5 | 5 | 5 | 5 |
| Decamethylcyclopentasiloxane | 3 | 3 | 3 | 3 | 3 | 3 |
| Texture in use — No slimy feel | ○ | ○ | ○ | ○ | Δ | ○ |
| Quick skin penetration | Δ | Δ | X | X | Δ | ○ |
| No stickiness | Δ | Δ | Δ | Δ | Δ | Δ |
| Emulsion stability | Δ | X | X | X | ○ | X |

As can be seen from the Table 2, all of the milky lotions of Examples 1 to 5 prepared using the organosiloxane derivatives as the compounds 1 to 5 that formed a gel structure in the organosiloxane derivative/higher alcohol/water were demonstrated to be excellent in texture in use in terms of the absence of slimy feel, quick skin penetration, and the absence of stickiness and to further have a relatively favorable emulsion stability.

By contrast, as can be seen from the Table 3, the milky lotions of Comparative Examples 1 to 4 formulated with the comparative compounds 1 to 4 that formed no gel structure in the organosiloxane derivative/higher alcohol/water had insufficient texture in use in terms of skin penetration and stickiness and were also inferior in emulsion stability. Moreover, the milky lotion of Comparative Example 5 formulated with the organosiloxane derivative as the compound 1 together with the higher fatty acid also had unsatisfactory texture in use in terms of slimy feel and skin penetration. Furthermore, the milky lotion of Comparative Example 6 comprising no higher alcohol combined therewith also had slight stickiness and was inferior particularly in emulsion stability.

These results demonstrated that a cosmetic excellent in texture in use, particularly in terms of the absence of slimy feel, quick skin penetration, and the absence of stickiness is obtained by incorporating the specifically structured organosiloxane derivative having a carboxyl group, a higher alcohol, and water together in the cosmetic.

Hereinafter, Formulation Examples of the cosmetic of the present invention formulated with the organosiloxane derivative, a higher alcohol, and water will be shown specifically. However, the present invention is not intended to be limited to them.

Formulation Example 1

Milky Lotion

| (Components) | (mass %) |
|---|---|
| (1) Ion-exchange water | Balance |
| (2) Trisodium edetate | 0.1 |
| (3) Phenoxy ethanol | 0.3 |
| (4) Butylene glycol | 7 |
| (5) Glycerin | 5 |
| (6) Carboxyvinyl polymer | 0.06 |
| (7) Potassium hydroxide | 0.04 |
| (8) Compound 1 | 0.8 |
| (9) Glyceryl stearate | 0.8 |
| (10) PEG-5 glyceryl stearate | 1.1 |

-continued

| (Components) | (mass %) |
|---|---|
| (11) Behenyl alcohol | 0.5 |
| (12) Dimethylpolysiloxane | 5 |
| (13) Decamethylcyclopentasiloxane | 5 |

(Production Method)

An oil and surfactant phase of the components (8) to (13) heated to 75° C. were gradually added to an aqueous phase of the components (1) to (7) heated to 75° C. The mixture was stirred using a homo mixer and then cooled to 30° C. to obtain a milky lotion.

Figure 2:
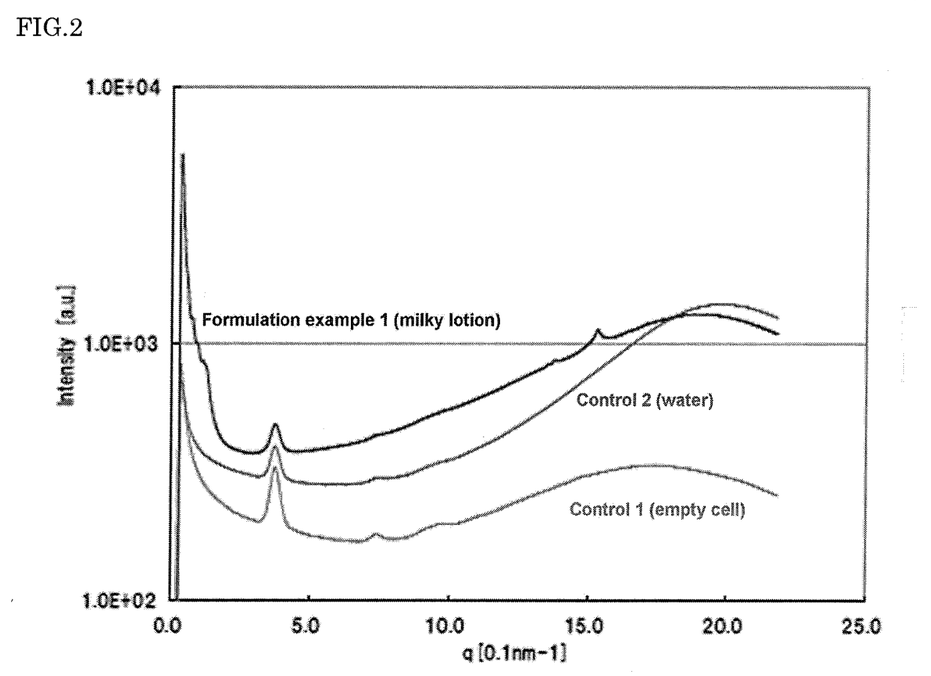
FIG. 2 shows results of small-angle X-ray scattering (SAXS) analysis of a lotion of Formulation Example 1.

This milky lotion of Formulation Example 1 was subjected to small-angle X-ray scattering measurement (conducted at 25° C. using Spring 8). The measurement results are shown in FIG. 2. In the diagram, controls 1 and 2 are spectra measured for comparison using a empty cell and water, respectively.

As shown in FIG. 2, a single peak specific to a gel structure was observed around q=15 in a wide-range region for the milky lotion of Formulation Example 1. This demonstrated that the milky lotion of Formulation Example 1 contains a gel structure formed by the organosiloxane derivative/higher alcohol/water.

Moreover, the milky lotion of Formulation Example 1 thus obtained was excellent in texture in use in terms of all of the absence of slimy feel, quick skin penetration, and the absence of stickiness and further had favorable emulsion stability.

Formulation Example 2

Milky Lotion

| (Components) | (mass %) |
|---|---|
| (1) Ion-exchange water | Balance |
| (2) Glycerin | 5 |
| (3) Butylene glycol | 5 |
| (4) Polyethylene glycol 1500 | 2 |
| (5) Ethanol | 3 |
| (6) Phenoxy ethanol | 0.3 |
| (7) Paraben | 0.1 |
| (8) Potassium hydroxide | 0.1 |
| (9) Trisodium edetate | 0.05 |
| (10) Carboxyvinyl polymer | 0.1 |
| (11) Xanthan Gum | 0.1 |
| (12) Behenyl alcohol | 0.5 |
| (13) Organosiloxane derivative (In the formula (1), $R^1 = CH_3$, $R^2$ to $R^3 = $ —O—Si(CH$_3$)$_3$, q = 8, and M = K) | 1 |
| (14) Petrolatum | 2 |
| (15) Squalan | 3 |
| (16) Decamethylcyclopentasiloxane | 3 |
| (17) Dimethylpolysiloxane | 2 |
| (18) Cetyl 2-ethylhexanoate | 2 |
| (19) PEG-60 glyceryl isostearate | 1 |
| (20) PEG-5 glyceryl stearate | 1 |
| (21) Perfume | 0.1 |

(Production Method)

An oil and surfactant phase of the components (12) to (21) heated to 75° C. were gradually added to an aqueous phase of the components (1) to (11) heated to 75° C. The mixture was stirred using a homo mixer and then cooled to 30° C. to obtain a milky lotion.

Formulation Example 3

Cream

| (Components) | (mass %) |
|---|---|
| (1) Ion-exchange water | Balance |
| (2) Glycerin | 7 |
| (3) Dipropylene glycol | 7 |
| (4) Erythritol | 1 |
| (5) Polyethylene glycol 20000 | 2 |
| (6) Phenoxy ethanol | 0.5 |
| (7) Triethanolamine | 0.5 |
| (8) Trisodium edetate | 0.1 |
| (9) Carboxyvinyl polymer | 0.1 |
| (10) Xanthan Gum | 0.1 |
| (11) Behenyl alcohol | 3 |
| (12) Stearyl alcohol | 1 |
| (13) Organosiloxane derivative (In the formula (1), $R^1 = CH_3$, $R^2$ to $R^3 = $ —O—Si(CH$_3$)$_3$, q = 16, and M = Na) | 1 |
| (14) Microcrystalline wax | 1 |
| (15) Petrolatum | 2 |
| (16) Squalan | 5 |
| (17) Decamethylcyclopentasiloxane | 3 |
| (18) Dimethylpolysiloxane | 3 |
| (19) Isononyl isononanoate | 2 |
| (20) PEG-60 glyceryl isostearate | 1 |
| (21) PEG-5 glyceryl stearate | 1 |
| (22) Perfume | 0.1 |

(Production Method)

An oil and surfactant phase of the components (11) to (22) heated to 75° C. were gradually added to an aqueous phase of the components (1) to (10) heated to 75° C. The mixture was stirred using a homo mixer and then cooled to 30° C. to obtain a cream.

Formulation Example 4

Sunscreen Cosmetic

| (Components) | (mass %) |
|---|---|
| (1) Polyoxyethylene hydrogenated castor oil | 1 |
| (2) Dimethicone copolyol | 0.5 |
| (3) Decamethylcyclopentasiloxane | 15 |
| (4) Organosiloxane derivative (In the formula (3), $R^9$ to $R^{12} = CH_3$, P = 6.6, q = 8, and M = K) | 0.5 |
| (5) Behenyl alcohol | 0.3 |
| (6) Phenyltrimethicone | 1 |
| (7) Hydrophobized titanium oxide | 5 |
| (8) Hydrophobized zinc oxide | 2 |
| (9) Spherical alkyl polyacrylate powder | 2 |
| (10) 2-Ethylhexyl p-methoxycinnamate | 5 |
| (11) Citric acid | 0.01 |
| (12) Sodium citrate | 0.09 |
| (13) Silica | 1 |
| (14) Paraben | Q.S. |
| (15) Phenoxy ethanol | Q.S. |
| (16) Sodium hydroxide | 0.05 |
| (17) Ethanol | 5 |
| (18) Dynamite glycerin | 1 |
| (19) Succinoglycan | 0.2 |
| (20) Cellulose gum | 1 |
| (21) Ion-exchange water | Balance |

(Production Method)

An aqueous phase of the components (11) to (21) was prepared. Then, an oil phase of the components (1) to (10) was gradually added thereto. Finally, the mixture was stirred using a homo mixer.

Formulation Example 5

Emulsion Foundation

| (Components) | (mass %) |
|---|---|
| (1) Talc | 3 |
| (2) Titanium dioxide | 4 |
| (3) Red iron oxide | 0.5 |
| (4) Yellow iron oxide | 1.5 |
| (5) Black iron oxide | 0.1 |
| (6) Bentonite | 0.5 |
| (7) Sorbitan POE monostearate | 1 |
| (8) Triethanolamine | 1.5 |
| (9) Dipropylene glycol | 8 |
| (10) Ion-exchange water | Balance |
| (11) Organosiloxane derivative (In the formula (3), $R^9$ to $R^{12}$ = $CH_3$, p = 1, q = 12, and M = Na) | 0.6 |
| (12) Stearyl alcohol | 0.4 |
| (13) Isohexadecyl alcohol | 6 |
| (14) Glyceryl monostearate | 2 |
| (15) Liquid lanolin | 2 |
| (16) Liquid paraffin | 6 |
| (17) Paraben | 0.1 |
| (18) Perfume | 0.05 |

(Production Method)

Dipropylene glycol containing bentonite dispersed therein was added to ion-exchanged water, and the mixture was stirred at 70° C. using a homo mixer. Then, the remaining aqueous phase components were added thereto, and the mixture was stirred. Sufficiently mixed and pulverized powder portions were added thereto with stirring, and the mixture was stirred at 70° C. Finally, an oil phase dissolved by heating to 70 to 80° C. was gradually added thereto, and the mixture was stirred using a homo mixer and then cooled to 30° C. to obtain an emulsified foundation.

Formulation Example 6

Emulsion Eye Shadow

| (Components) | (mass %) |
|---|---|
| (1) Talc | 10 |
| (2) Kaolin | 2 |
| (3) Pigment | 5 |
| (4) Organosiloxane derivative (In the formula (1), $R^1$ to $R^3$ = —O—Si($R^5$)$_2$—$X^i$, $R^5$ = $CH_3$, $R^6$ = $C_8H_{17}$, $R^7$ to $R^8$ = $CH_3$, ai = 1, $X^{i+1}$ = $CH_3$, q = 8, M = $HN^+(CH_2CH_3OH)_3$) | 1 |
| (5) Behenyl alcohol | 0.2 |
| (6) Isopropyl myristate | 6 |
| (7) Liquid paraffin | 5 |
| (8) Propylene glycol monolaurate | 3 |
| (9) Perfume | 0.05 |
| (10) Ion-exchange water | Balance |
| (11) Butylene glycol | 5 |
| (12) Glycerin | 1 |
| (13) Potassium hydroxide | 0.07 |
| (14) Phenoxy ethanol | 0.5 |
| (15) Disodium edetate | 0.1 |

(Production Method)

The powder portions (1) to (3) were mixed and then pulverized. The aqueous phase portions (10) to (15) were heated to 75° C. The oil phase portions (4) to (9) were dissolved by heating to 80° C. The powder portions were added to the aqueous phase, and the mixture was stirred. The oil phase was gradually added thereto with stirring, followed by homo mixer treatment. The mixture was cooled to 30° C. to obtain an emulsified eye shadow.

What is claimed is:

1. A gel composition comprising:
an organosiloxane compound of the following formula (1) or (3),
a monohydric aliphatic alcohol having 10 to 30 carbon atoms, and water;

(1)

in the formula (1), at least one of $R^1$ to $R^3$ is a functional group of —O—Si($R^4$)$_3$ in which $R^4$ is an alkyl group having 1 to 6 carbon atoms or a phenyl group, or a functional group of —O—Si($R^5$)$_2$—$X^1$ in which $R^5$ is an alkyl group having 1 to 6 carbon atoms or a phenyl group, and $X^1$ is a functional group of the following formula (2) when i=1; and the remaining $R^1$ to $R^3$ may be the same or different and each may be a substituted or unsubstituted monovalent hydrocarbon group; M is a hydrogen atom, a metal atom, or an organic cation; A is a linear or branched alkylene group of $C_qH_{2q}$ in which q is any integer of 0 to 20; and the organosiloxane compound of the formula (1) contains a total of 2 to 20 silicon atoms (Si) on average per molecule;

(2)

in the formula (2), $R^6$ is a hydrogen atom, an alkyl group having 1 to 6 carbon atoms, or a phenyl group; $R^7$ and $R^8$ are selected from an alkyl group having 1 to 6 carbon atoms or a phenyl group; B is a linear or branched alkylene group of $C_rH_{2r}$ which may be partially branched in which r is any integer of 2 to 20; and i specifies the generation of a silylalkyl group of $X^i$ and is any integer of 1 to n when the generation number is n, wherein the generation number n is any integer of 1 to 10; ai is any integer of 0 to 2 when i is 1, or ai is an integer smaller than 3 when i is 2 or larger; and $X^{i+1}$ is the silylalkyl group when i is smaller than n, and is a methyl group when i=n;

(3)

in the formula (3), $R^9$ to $R^{12}$ may be the same or different and are selected from a substituted or unsubstituted monovalent hydrocarbon group; M is a hydrogen atom, a metal atom, or an organic cation; Q is a linear or branched alkylene group of $C_qH_{2q}$ in which q is any integer of 0 to 20; and p is any number of 0 to 20, wherein a molar ratio of the organosiloxane compound: the monohydric aliphatic alcohol is in the range of 1:0.1 to 1:30, an amount of water is in the range of 100 to 10000 parts by mass with respect to 100 parts by mass of the mixture of the organosiloxane compound and the monohydric aliphatic alcohol, and the gel composition contains crystal structure characterized in that bilayer membranes of the organosiloxane compound and the monohydric aliphatic alcohol are arranged in a layer form in a long-period structure and the hydrophobic groups of the organosiloxane compound and the monohydric aliphatic alcohol are arranged in a hexagonal form on the short-plane side.

2. The gel composition according to claim 1, wherein the organosiloxane compound is of the formula (1), and $R^1$ and $R^2$ are selected from a functional group of —O—Si$(R^4)_3$ in which $R^4$ is an alkyl group having 1 to 6 carbon atoms; $R^3$ is a monovalent hydrocarbon group having 1 to 10 carbon atoms; and q is any integer of 6 to 20.

3. The gel composition according to claim 1, the organosiloxane compound is of the formula (3), wherein $R^9$ to $R^{12}$ are a group selected from the group consisting of substituted or unsubstituted alkyl groups having 1 to 20 carbon atoms, aryl groups, and aralkyl groups; q is any integer of 6 to 20; p is any number of 1 to 20; and M is an atom selected from the group consisting of hydrogen, alkali metal, and alkaline-earth metal atoms.

4. The gel composition according to claim 1, wherein the monohydric aliphatic alcohol having 10 to 30 carbon atoms is an aliphatic alcohol having a melting point of 40° C. or higher.

5. A cosmetic comprising;
an organosiloxane compound of the formula (1) or (3):
a monohydric aliphatic alcohol having 10 to 30 carbon atoms, and water;

in the formula (1), at least one of $R^1$ to $R^3$ is a functional group of —O—Si$(R^4)_3$ in which $R^4$ is an alkyl group having 1 to 6 carbon atoms or a phenyl group, or a functional group of —O—Si$(R^5)_2$—$X^1$ in which $R^5$ is an alkyl group having 1 to 6 carbon atoms or a phenyl group, and $X^1$ is a functional group of the following formula (2) when i=1; and the remaining $R^1$ to $R^3$ may be the same or different and each may be a substituted or unsubstituted monovalent hydrocarbon group; M is a hydrogen atom, a metal atom, or an organic cation; A is a linear or branched alkylene group of $C_qH_{2q}$ in which q is any integer of 0 to 20; and the organosiloxane compound of the formula (1) contains a total of 2 to 20 silicon atoms (Si) on average per molecule;

in the formula (2), $R^6$ is a hydrogen atom, an alkyl group having 1 to 6 carbon atoms, or a phenyl group; $R^7$ and $R^8$ are selected from an alkyl group having 1 to 6 carbon atoms or a phenyl group; B is a linear or branched alkylene group of $C_rH_{2r}$ which may be partially branched in which r is any integer of 2 to 20; and i specifies the generation of a silylalkyl group of $X^i$ and is any integer of 1 to n when the generation number is n, wherein the generation number n is any integer of 1 to 10; ai is any integer of 0 to 2 when i is 1, or ai is an integer smaller than 3 when i is 2 or larger; and $X^{i+1}$ is the silylalkyl group when i is smaller than n, and is a methyl group when i=n;

in the formula (3), $R^9$ to $R^{12}$ may be the same or different and are selected from a substituted or unsubstituted monovalent hydrocarbon group; M is a hydrogen atom, a metal atom, or an organic cation; Q is a linear or branched alkylene group of $C_qH_{2q}$ in which q is any integer of 0 to 20; and p is any number of 0 to 20;

wherein a system consisting of the organosiloxane compound/higher alcohol/water forms a gel structure, a molar ratio of the organosiloxane compound: the monohydric aliphatic alcohol is in the range of 1:0.1 to 1:30, an amount of water is in the range of 100 to 10000 parts by mass with respect to 100 parts by mass of the mixture of the organosiloxane compound and the monohydric aliphatic alcohol, and the gel composition contains crystal structure characterized in that bilayer membranes of the organosiloxane compound and the monohydric aliphatic alcohol are arranged in a layer form in a long-period structure and the hydrophobic groups of the organosiloxane compound and the monohydric aliphatic alcohol are arranged in a hexagonal form on the short-plane side.

6. The cosmetic according to claim 5, wherein the organosiloxane compound is of the formula (1), and $R^1$ and $R^2$ are selected from a functional group of —O—Si$(R^4)_3$ in which $R^4$ is an alkyl group having 1 to 6 carbon atoms; $R^3$ is a monovalent hydrocarbon group having 1 to 10 carbon atoms; and q is any integer of 6 to 20.

7. The cosmetic according to claim 5, wherein the organosiloxane compound is of the formula (1), and at least one or more of $R^1$ to $R^3$ are selected from a functional group of the following formula (4) or (5):

and the remaining $R^1$ to $R^3$ may be the same or different and are selected from a substituted or unsubstituted monovalent hydrocarbon group.

8. The cosmetic according to claim 5, wherein the organosiloxane compound is of the formula (3), and $R^9$ to $R^{12}$ are a group selected from the group consisting of substituted or unsubstituted alkyl groups having 1 to 20 carbon atoms, aryl groups, and aralkyl groups; q is any integer of 6 to 20; p is any number of 1 to 20; and M is an atom selected from the group consisting of hydrogen, alkali metal, and alkaline-earth metal atoms.

9. The cosmetic according to claim 5, wherein the monohydric aliphatic alcohol having 10 to 30 carbon atoms is an aliphatic alcohol having a melting point of 40° C. or higher.

10. The gel composition according to claim 2, wherein the monohydric aliphatic alcohol having 10 to 30 carbon atoms is an aliphatic alcohol having a melting point of 40° C. or higher.

11. The gel composition according to claim 3, wherein the monohydric aliphatic alcohol having 10 to 30 carbon atoms is an aliphatic alcohol having a melting point of 40° C. or higher.

12. The cosmetic according to claim 6, wherein the monohydric aliphatic alcohol having 10 to 30 carbon atoms is an aliphatic alcohol having a melting point of 40° C. or higher.

13. The cosmetic according to claim 7, wherein the monohydric aliphatic alcohol having 10 to 30 carbon atoms is an aliphatic alcohol having a melting point of 40° C. or higher.

14. The cosmetic according to claim 8, wherein the monohydric aliphatic alcohol having 10 to 30 carbon atoms is an aliphatic alcohol having a melting point of 40° C. or higher.

15. A gel composition comprising:
an organosiloxane compound of the following formula (1),
a monohydric aliphatic alcohol having 10 to 30 carbon atoms, and water, in the formula (1), at least one of $R^1$ to $R^3$ is a functional group of $-O-Si(R^4)_3$ in which $R^4$ is an alkyl group having 1 to 6 carbon atoms or a phenyl group, or a functional group of $-O-Si(R^5)_2-X^1$ in which $R^5$ is an alkyl group having 1 to 6 carbon atoms or a phenyl group, and $X^1$ is a functional group of the following formula (2) when i=1; and the remaining $R^1$ to $R^3$ may be the same or different and each may be a substituted or unsubstituted monovalent hydrocarbon group; M is a hydrogen atom, a metal atom, or an organic cation; A is a linear or branched alkylene group of $C_qH_{2q}$ in which q is any integer of 0 to 20; and the organosiloxane compound of the formula (1) contains a total of 2 to 20 silicon atoms (Si) on average per molecule;

in the formula (2), $R^6$ is a hydrogen atom, an alkyl group having 1 to 6 carbon atoms, or a phenyl group; $R^7$ and $R^8$ are selected from an alkyl group having 1 to 6 carbon atoms or a phenyl group; B is a linear or branched alkylene group of $C_rH_{2r}$, which may be partially branched in which r is any integer of 2 to 20; and i specifies the generation of a silylalkyl group of $X^i$ and is any integer of 1 to n when the generation number is n, wherein the generation number n is any integer of 1 to 10; ai is any integer of 0 to 2 when i is 1, or ai is an integer smaller than 3 when i is 2 or larger; and $X^{i+1}$ is the silylalkyl group when i is smaller than n, and is a methyl group when i=n, wherein at least one or more of $R^1$ to $R^3$ are selected from a functional group of the following formula (4) or (5):

and the remaining $R^1$ to $R^3$ may be the same or different and are selected from a substituted or unsubstituted monovalent hydrocarbon group.

16. The gel composition according to claim 15, wherein the monohydric aliphatic alcohol having 10 to 30 carbon atoms is an aliphatic alcohol having a melting point of 40° C. or higher.

* * * * *